United States Patent [19]

Easley et al.

[11] Patent Number: 5,203,353
[45] Date of Patent: Apr. 20, 1993

[54] METHOD OF PENETRATING AND WORKING IN THE VITREOUS HUMOR OF THE EYE

[75] Inventors: James C. Easley, St. Charles; Kurt W. Gampp, Jr., Ellisville; Gregg D. Scheller, Ballwin, all of Mo.

[73] Assignee: Surgical Technologies, Inc., Chesterfield, Mo.

[21] Appl. No.: 816,802

[22] Filed: Jan. 3, 1992

Related U.S. Application Data

[62] Division of Ser. No. 425,936, Oct. 24, 1989, Pat. No. 5,078,712.

[51] Int. Cl.$^5$ ............................................. A61B 17/36
[52] U.S. Cl. ..................................... 128/898; 606/15; 606/50; 606/4
[58] Field of Search ............... 606/4, 7, 15, 16, 48, 606/50; 604/902; 128/898

[56] References Cited

U.S. PATENT DOCUMENTS

| | | | |
|---|---|---|---|
| 4,122,853 | 10/1978 | Smith | 606/4 |
| 4,483,338 | 11/1984 | Bloom et al. | 606/50 |
| 4,537,193 | 8/1985 | Tanner | 128/398 X |
| 4,583,539 | 4/1986 | Karlin et al. | 606/4 |
| 4,674,499 | 6/1987 | Pao | 606/50 |
| 4,820,264 | 4/1989 | Matsui et al. | 606/4 X |

*Primary Examiner*—Michael H. Thaler
*Attorney, Agent, or Firm*—Polster, Lieder, Woodruff & Lucchesi

[57] ABSTRACT

A surgical instrument for use in penetrating and working in the vitreous humor of an eye comprises a finger grip member and a rigid needle extending from the finger grip member, with a single continuous fiber optic member extending from a distal end of the needle through the needle and the finger grip member to a cone shaped proximal end contained in a large connecting member constructed of heat conductive material. The surgical instrument includes a stripping tool at its distal end that is bent at a right angle and positioned in a plane that is parallel to the longitudinal axis of the needle but does not intersect this axis. The surgical instrument also comprises an infusion/aspiration system including a hollow pipe attached to the needle that extends parallel to the longitudinal axis of the needle but does not interfere with a beam of light projected from the distal end of the fiber optic member extending through the needle. The instrument also includes a coaxial bipolar diathermy comprising an exterior needle surrounding and coaxial to the fiber optic needle, the exterior needle being insulated from the interior fiber optic needle and both needles being electrically connected to a conventional radio frequency generator for creating an electric potential between the distal ends of the interior and exterior needles for use in coagulating bleeding vessels on a retinal surface or beneath pre-retinal membranes.

2 Claims, 3 Drawing Sheets

METHOD OF PENETRATING AND WORKING IN THE VITREOUS HUMOR OF THE EYE

This is a divisional of copending application Ser. No. 07/425,936 filed on Oct. 24, 1989, now U.S. Pat. No. 5,078,712.

BACKGROUND OF THE INVENTION

(1) Field of the Invention

The present invention relates to tissue manipulators for use in vitreous surgery, in particular, a tissue manipulator that combines a fiber optic endoilluminator with a coaxial bipolar diathermy and an infusion/aspiration system.

(2) Description of the Related Art

Vitreous surgery tissue manipulators of the type provided by the present invention commonly comprise a hand-held piece having a hollow needle extending from one end. A plurality of parallel fiber optic members extend through the hand piece and the hollow needle, and terminate at distal ends adjacent the distal end of the needle. The proximal end of the tissue manipulator hand piece is connected to a light conducting member that conveys light from an external light source to the manipulator. The light conducting member illuminates the proximal ends of the fiber optic members extending through the tissue manipulator, causing a beam of light to be directed outwardly from the distal ends of the fiber optic members adjacent the distal end of the needle.

Because the tissue manipulator needle is used by penetrating the needle into the vitreous humor of an eye, the external dimensions of the needle must be kept as small as possible. This, in turn, limits the cross-sectional diameter of the bore through the needle and the number of fiber optic members extending through the needle bore.

Each of the fiber optic members extending through the manipulator hand piece and needle is surrounded by a non-light conducting cladding. The cladding directs the light illuminating the proximal ends of the fiber optic members through the members and out their distal ends. A disadvantage of this type of conventional tissue manipulator is that much of the cross-sectional area of the fiber optic members extending through the needle bore is taken up by the cladding surrounding each of the members and the gap between adjacent members, reducing the actual amount of cross-sectional area of the needle bore that is taken up by the light conveying optic fibers.

Many conventional tissue manipulators are provided with a membrane pic extending from the distal end of the manipulator needle. The pic is used for engaging tissues in the vitreous humor of an eye and for retinal membrane stripping. The pics are commonly formed by grinding down the distal ends of the manipulator needle until only a narrow portion of the needle side wall remains. This narrow portion of side wall is then given a general triangular shape, with a section of the narrow side wall adjacent the apex of the triangle being bent over at a 45° angle into the projected path of light from the distal end of the fiber optic members extending through the needle.

Because the side walls of the needles are made very thin to devote as much of the cross-sectional area available to the fiber optic members, a membrane pic formed in the above-described manner from the thin side walls of the needle will tend to bend or break over a period of use. Additionally, because the membrane pic is bent at a 45° angle into the projected path of light from the distal end of the needle, the light beam will often reflect off of the interior surface of the pic and the membrane pic itself will often cast a shadow on the retinal surface adjacent the pic, making it difficult for the pic user to observe the end of the pic and the retinal surface adjacent the pic.

Often, in performing vitreous surgery, a separate infusion or aspiration needle is needed to supply infusion fluid or suction, respectively. When infusion or aspiration is required in vitreous surgery, a third hand for operating the infusion or aspiration system is also often required.

Moreover, in performing vitreous surgery, it is often necessary to coagulate bleeding vessels either on a retinal surface or beneath pre-retinal membranes. This situation requires the use of a separate manual bipolar diathermy instrument to stop the bleeding. When use of the diathermy instrument is necessary, an additional hand is often required to manipulate the instrument.

It is an object of the present invention to overcome the disadvantages associated with prior art tissue manipulators by providing a surgical instrument for use in vitreous surgery that combines a more efficient fiber optic endoilluminator membrane pic with a coaxial bipolar diathermy or an infusion/aspiration system in a single instrument.

It is a further object of the present invention to provide a fiber optic endoilluminator with an increased illumination capability over the prior art illuminators having the same cross-sectional area.

It is a further object of the present invention to provide a fiber optic light conveying member that projects an increased amount of illumination from its distal end than prior art fiber optic members having the same cross-sectional diameter at their distal ends due to an improved light gathering configuration of the proximal end of the fiber optic member that is subjected to a source of illumination.

It is also an object of the present invention to provide a tissue manipulator pic that is stronger than prior art membrane pics and does not reflect the beam of light projected from the endoilluminator or cast shadows on the retinal surface.

It is a still further object of the present invention to provide a connector at the proximal end of the light conveying fiber optic member that absorbs heat radiated by the source of illumination and conveys the heat away from the proximal end of the fiber optic member.

SUMMARY OF THE INVENTION

The vitreous surgery tissue manipulator of the present invention is comprised of a hand-held finger-grip member with at least one conduit extending through the member, a hollow manipulator needle secured in the conduit at a distal end of the grip member, and a light conveying fiber optic member inserted in the conduit at a proximal end of the grip member. The grip member conduit and a hollow bore extending through the needle are coaxial and communicate with each other.

A single continuous light conveying fiber optic member extends from a source of light to the tissue manipulator. The fiber optic member is inserted into the grip member conduit at the proximal end of the finger grip member, and extends through the conduit and the needle bore to its distal end. The distal end of the fiber optic member is coplanar with the distal end of the needle. The single fiber optic member, having a given cross-sectional diameter, conveys a substantially increased amount of illumination from the source of light to the distal end of the fiber optic member than do the prior art bundles of fiber optic members having substantially the same cross-sectional diameter.

The fiber optic member of the present invention exits from the proximal end of the tissue manipulator and extends through a protective flexible tube to a connector plug at the proximal end of the fiber optic member. The connector plug is formed from a mass of heat conducting material, such as aluminum or copper, and couples the proximal end of the fiber optic member to a conventional source of illumination for the tissue manipulator. The connector receives heat at its proximal end from the source of illumination and conveys the heat away from the proximal end of the fiber optic member. The heat received is conducted away from the fiber optic member and the source of illumination, and is convected away from the connector plug and illumination source.

The fiber optic member extends through the connector to its proximal end. The proximal end of the fiber optic member and the proximal end of the connector are coplanar. A portion of the fiber optic member contained in the connector is modified into the shape of a truncated cone. The proximal end of the fiber optic member has an increased diameter than the remainder of the member and forms the base of the cone. The cone tapers from its base at the proximal end of the fiber optic member toward a reduced diameter apex having a diameter equal to the diameter of the remaining portion of the fiber optic member. The increased diameter cone base at the proximal end of the fiber optic member receives and conveys through the fiber optic member an increased amount of illumination from the light source than do conventional fiber optic members having a substantially constant diameter along their entire lengths.

In one embodiment of the invention, the continuous cross-sectional diameter of the fiber optic member between its proximal and distal ends is less than the cross-sectional diameter of the finger grip member conduit and the cross-sectional diameter of the needle bore through which it extends. The difference in cross-sectional diameters creates an open passage running parallel with the fiber optic member through the tissue manipulator grip member and needle.

A proximal end of the open passage adjacent the proximal end of the tissue manipulator is adapted to be connected with a selectively supplied external source of fluid or suction such as a saline solution or a viscoelastic liquid, or a conventional aspiration system, respectively. This structure permits the selective supply of a liquid or suction through the open passage formed through the finger grip member and manipulator needle to the distal end of the needle. The fluid dispensed from the distal end of the needle can be used to move membranes or flush blood and debris and other tissues from the retinal surface where vitreous surgery is taking place. The suction provided at the distal end of the needle can be used to aspirate membranes, tissues and other debris into the needle distal end.

In a similar embodiment to the one described above, a rigid tube having three sections is attached to the exterior surface of the manipulator needle. A main section of the tube runs parallel with the manipulator needle and terminates in a bent section that extends a slight distance from the distal end of the needle. The bent section of the tube extends from the main section at an angle of 45° to the longitudinal axis of the needle, and does not protrude into the direct path of a beam of light projected from the distal end of the fiber optic member and the distal end of the needle. The opposite end of the main tube section is also connected to a bent section that extends outward at an angle of about 45° from the axis of the needle and the finger grip member. This end of the rigid tube is adapted to be connected with an exterior source of selectively supplied fluid or aspiration. On selective supply of pressurized fluid to this end of the rigid tube, the fluid is conveyed through the tube and is dispensed from the bent section of the tube adjacent the distal end of the needle. Again, the pressurized fluid conveyed through the tube can be used in moving tissues or membranes, or localized flushing of blood and debris from the retinal surface where vitreous surgery is taking place. The suction selectively provided at the distal end of the bent section of the tube can be used to aspirate membranes, tissues and other debris into the tube.

The distal end of the needle may also be provided with a pic that extends a slight distance beyond the distal end of the needle. The pic is formed from a rigid wire connected to the exterior surface of the needle. The wire extends parallel to the needle a slight distance beyond the distal end of the needle, and is bent at a right angle at its distal end. The bend in the distal end of the wire is oriented so that it will not protrude into the direct path of a beam of light projected from the distal end of the fiber optic member at the distal end of the needle. The positioning of the wire and the diameter of the wire being smaller than the diameter of the light conducting fiber optic member eliminates the pic reflection and shadow problems encountered with conventional tissue membrane pics, while still permitting a small amount of indirect light projected from the fiber optic member to illuminate the wire pic distal end, enabling the user of the pic to see the pic in the vitreous humor of an eye.

In addition, the cross-section of the bent distal end of the wire pic is shaped as an ellipse, with the major axis of the ellipse extending parallel to the longitudinal axis of the tissue manipulator grip member and needle. Providing the distal end of the wire pic with an elliptical cross-section improves the usefulness of the membrane pic in retinal membrane stripping. Moreover, by forming the membrane pic from a separate piece of rigid wire, the strength of the pic is substantially increased over conventional membrane pics formed by grinding down and bending over a side wall of the tissue manipulator needle.

A further embodiment of the present invention includes a tissue manipulator comprising a coaxial bipolar diathermy system. This manipulator comprises a hollow needle with a fiber optic member extending through its length as in the embodiments described above, and also includes an exterior metal tube coaxial to and surrounding the manipulator needle. The exterior tube is separated from the interior manipulator needle by an insulating material that completely surrounds the exterior surface of the interior needle. The needle and the exterior tube are electrically connected to a radio frequency generator and are selectively subjected to electric charges of different polarities, creating an electrical potential between the distal end of the needle and the distal end of the exterior tube. The potential created at the distal end of the needle and tube is used in diathermy coagulation of bleeding vessels either on the retinal surface or beneath pre-retinal membranes.

BRIEF DESCRIPTION OF THE DRAWINGS

Further objects and features of the present invention are revealed in the following detailed description of the preferred embodiments of the invention and in the drawing figures wherein.

DETAILED DESCRIPTION OF THE PREFERRED EMBODIMENT

Figure 1:
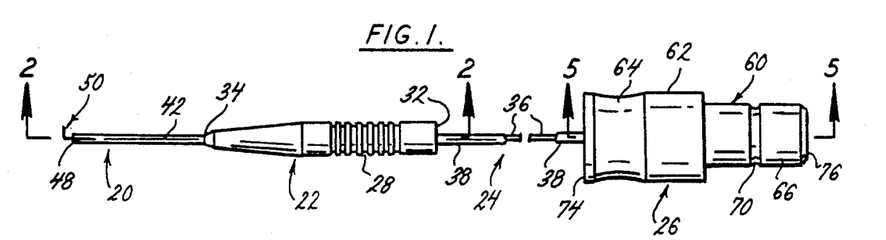
FIG. 1 is a segmented perspective view of the vitreous surgery tissue manipulator of the present invention.

FIG. 1 shows the component parts of the vitreous surgery tissue manipulator of the present invention. The tissue manipulator includes a needle portion 20, a finger grip member 22, a flexible fiber optic connection 24, and an illumination source connecting member 26.

Figure 2:
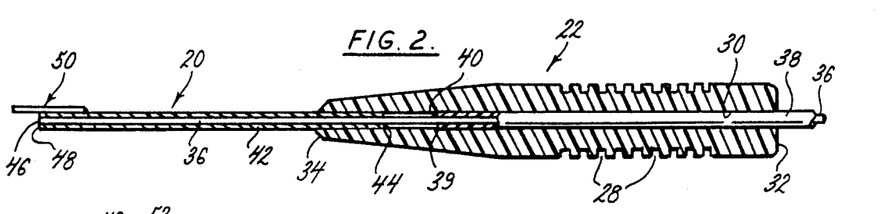
FIG. 2 is a side elevation view in section of the finger grip portion and needle portion of the tissue manipulator of the present invention.

A cross-sectional view of the general structure the needle portion 20 and finger grip portion 22 of the tissue manipulator is shown in FIG. 2. The finger grip portion 22 is generally cylindrical and is formed with a series of serrations 28 formed around the exterior of the member that facilitate the gripping and manipulating of the member. A hollow conduit 30 extends through the grip portion 22 between its proximal 32 and distal 34 ends. The flexible fiber optic connection 24 is inserted into the conduit 30 at the proximal end 32 of the grip portion. The needle portion 20 is inserted into the conduit 30 at the distal end 34 of the grip portion.

As seen in FIG. 2, the flexible fiber optic connection 24 is comprised of a continuous single fiber optic member 36 surrounded by a flexible, protective, insulation 38. The conduit 30 is counterbored so that it has two different internal diameters that meet at an abutment 39, the larger diameter being sized to receive the fiber optic member and its surrounding insulation. The insulation 38 of the fiber optic connection 24 terminates at a distal end 40 intermediate the grip portion conduit 30 at the abutment 39 where the larger diameter counterbore ends and the smaller diameter portion of the conduit 30 begins. The proximal end of the connection 24 terminates intermediate a connector plug to be described later.

The needle portion 20 is comprised of a hollow tubular stainless steel needle 42 inserted into the conduit 30 at the distal end 34 of the finger grip portion 22. The needle 42 terminates at a proximal end 44 intermediate the smaller diameter portion of the conduit 30, spaced from the distal end 40 of the fiber optic insulation 38. The fiber optic member 36 contained within the insulation 38 extends beyond the distal end 40 of the insulation, through the reduced diameter portion of the conduit 30 to the needle proximal end 44, and through the interior bore of the needle 42. The distal end 46 of the fiber optic member 36 terminates at the distal end 48 of the needle 42.

Figure 3:
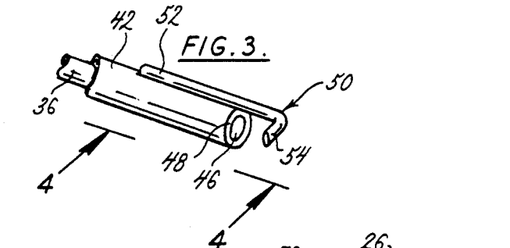
FIG. 3 is a segmented perspective view of the details of the stripping pic and distal end of the tissue manipulator needle.
Figure 4:
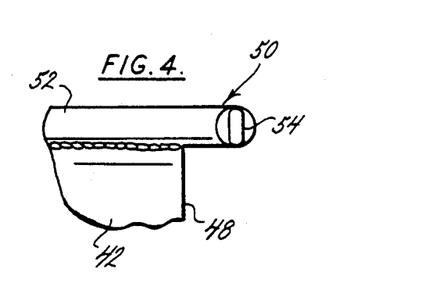
FIG. 4 is a segmented perspective view of the details of the stripping pic at the needle distal end.

A membrane stripping tool or pic 50 is also provided at the distal end 48 of the needle. The pic 50 is constructed of a rigid wire that is preferably bent at a right angle between a proximal section 52 and a distal section 54. The wire sections may be bent at a different angle if desired The proximal section 52 of the wire is secured to the exterior surface of the needle adjacent the distal end 48 and parallel to the longitudinal axis of the needle. The proximal end 52 of the stripping tool can be secured to the exterior surface of the needle 42 by welding, brazing or some other equivalent means. The wire and the weld between the wire and the needle exterior surface are machined to present a smooth surface at the join between the wire and needle surface. The distal end 54 of the tool 50 is bent at a right angle and is positioned relative to the distal end 46 of the fiber optic member 36 so that it will not extend into a projected path of light from the distal end 46 of the fiber optic member.

As seen in FIGS. 3 and 4, the proximal and distal ends 52, 54 of the stripping tool 50 are bent at a right angle and are positioned in a plane that is parallel to the longitudinal axis of the needle 42 and spaced slightly above this axis. This positioning of the stripping tool 50 prevents the direct light projected from the distal end 46 of the fiber optic member 36 from reflecting back off of the distal end 54 of the stripping tool, and prevents the distal end 54 of the stripping tool from casting a shadow on the retinal surface illuminated by a beam of light projected from the distal end 46 of the fiber optic member 36. Some of the indirect light projected from the distal end of the fiber optic member illuminates the distal end of the tool to enable the tool user to see the tool in the vitreous humor of an eye. Any reflection of the indirect light does not interfere with the vision of the user and any shadow of the tool will not be in the area of the work being performed with the tool.

The distal end 54 of the stripping tool 50 is also worked so that its cross-section is in the form of an ellipse, with the minor axis of the ellipse being parallel to the longitudinal axis of the needle 42. The ellipse minor axis is also contained in a plane containing the proximal section 52 and distal section 54 of the stripping tool. The elliptical cross-section of the distal end 54 of the stripping tool 50 enhances its usefulness in removing tissues from the retinal surface of an eye.

Figure 5:
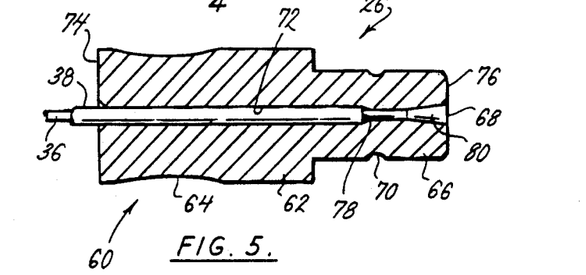
FIG. 5 is a side view in section of the light source connector at the proximal end of the tissue manipulator of the present invention.

At the proximal end of the flexible fiber optic connection 24 is the illumination source connector 26. The connector includes a plug 60 that is formed from a large amount of material having a high thermal conductivity. The larger size of the plug enhances its ability to conduct heat from an illumination source away from the fiber optic member contained in the plug. The exterior of the plug 60 is formed as two generally cylindrical sections with different diameters.

A first section 62 of the plug exterior has the larger diameter and is formed with a slight recess 64 in the circumference of the exterior surface. The recess 64 is provided to be gripped by an instrument operator to facilitate the insertion and removal of the connector plug 60 from a source of illumination.

The reduced diameter section 66 of the plug connector 60 is dimensioned to be inserted into an access opening of a conventional source of illumination to subject the proximal end 68 of the fiber optic member 36 to the source of illumination. The smaller plug section 66 is also provided with a recess 70 around its exterior surface to facilitate in the connection between the plug and the illumination source into which it is inserted.

The connector plug 60 includes a conduit 72 extending through the plug between its distal 74 and proximal 76 ends. The proximal end of the fiber optic member 36 and its surrounding protective insulation 38 are inserted into the conduit 72 at the distal end 74 of the plug. The flexible insulation 38 of the fiber optic member 36 terminates at a proximal end 78 intermediate the conduit 72 of the plug. The fiber optic member 36 extends completely through the conduit 72 of the plug to the proximal end 68 of the fiber optic member, coplanar with the proximal end 76 of the plug.

A portion of the fiber optic member 36 adjacent its proximal end 68 is formed in the shape of a truncated cone 80. In the preferred embodiment, the length of the truncated cone 80 is 0.200 of an inch long, with the diameter of the cone base 68 being 0.040 of an inch and the diameter of the cone apex 82 being 0.030 of an inch. The diameter of the cone apex is substantially the same diameter as the continuous fiber optic member 36 extending between the cone apex 82 and the distal end 46 of the fiber optic member.

The cone shape 80 provided at the proximal end of the fiber optic member 36 enhances the ability of the proximal end 68 of the fiber optic member to absorb light from the source of illumination into which the plug connector 60 is inserted. For cone sections of different lengths, it is found that forming the base of the cone by increasing the radius of the fiber optic member distal end by 0.025 times the length of the cone gives the most beneficial results.

The connector plug 60 itself is formed from a substantial amount of a high heat conducting material such as aluminum. The increased mass of the connector plug 60 enhances its ability to convey heat radiated from the source of illumination, away from the fiber optic member 36 and the source of illumination. The smaller section 56 of the plug is inserted into an access opening of the source of illumination and absorbs heat radiated and convected by the source of illumination. The heat absorbed by the small plug section 66 is conducted through the connector plug away from the fiber optic member 36 and toward the large plug section 62. Heat conducted to the large plug section 62 is then convected away from the connector plug 60 outside the source of illumination. In this manner the fiber optic member 36 and its insulation 38 are protected from the heat radiated and convected from an intense source of illumination.

Figure 6:
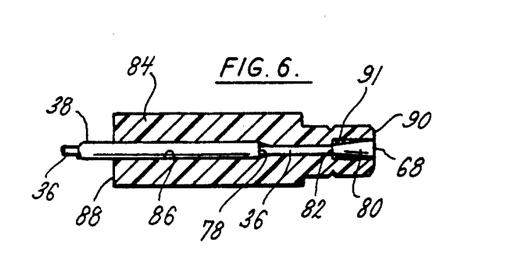
FIG. 6 is a side view in section of another light source connector at the proximal end of the tissue manipulator of the present invention.

FIG. 6 shows another embodiment of the connector plug 84 for connecting the proximal end 68 of the flexible fiber optic connection 24 of the present invention to a conventional source of illumination. As can be seen from the drawing figure, the relationship between the proximal end of the fiber optic connection 24 and the connector 84 is substantially the same as that disclosed with reference to FIG. 5.

In FIG. 6, the flexible fiber optic connection 24 is inserted into a conduit 86 extending through the connector 84 at a distal end 88 of the connector. The flexible insulation 38 of the fiber optic connection 24 terminates at its proximal end 78 intermediate the plug conduit 86. The proximal end 68 of the fiber optic member 36 ends coplanar with the proximal end 90 of the plug 84. Here, the fiber optic member 36 adjacent its proximal end is again formed as a truncated cone section 80. The base of the cone is coplanar with the proximal end 68 of the fiber optic member 36 and the proximal end 90 of the connector 84, and the apex 82 of the cone has the same diameter as the continuous length of the fiber optic member 36 extending from the cone apex 82 to the distal end of the fiber optic member 46. A short length of silicone rubber tubing 91 surrounds the cone section of the fiber optic member and is press-fit into a counterbored portion of the conduit 86 adjacent the proximal end 90 of the plug. The silicone tubing 91 holds the cone section of the fiber optic member in the plug conduit. This type of connector may be used where it is not necessary to conduct heat from an intense source of illumination away from the fiber optic member.

Figure 7:
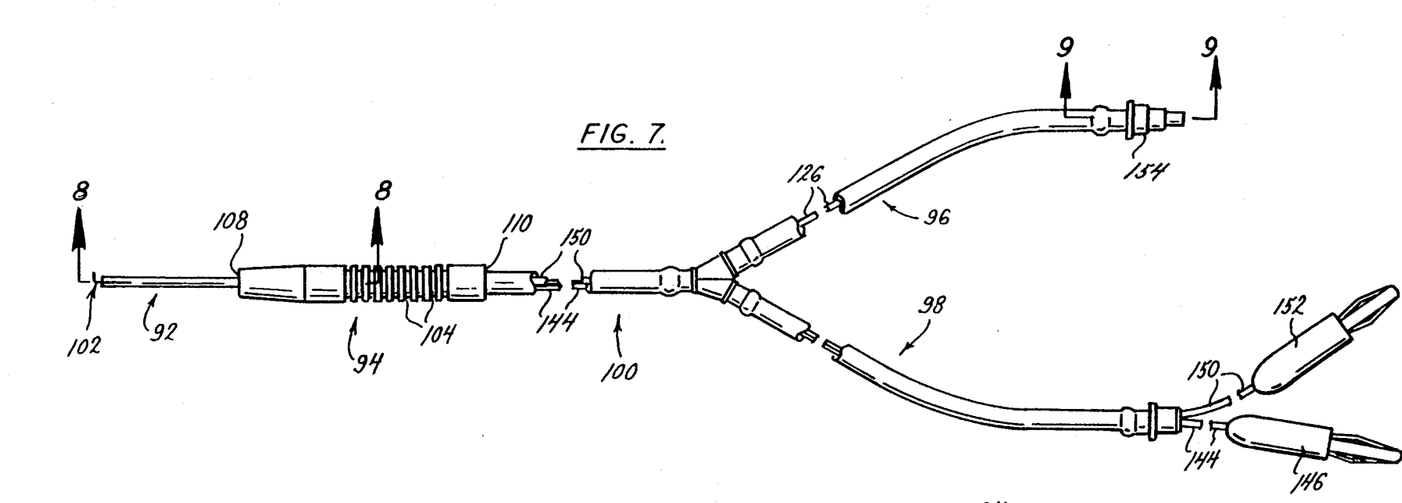
FIG. 7 is a segmented perspective view of the component parts of the tissue manipulator of the present invention comprising a coaxial bipolar diathermy.

FIG. 7 shows an embodiment of the present invention that incorporates a coaxial bipolar diathermy into the structure of the tissue manipulator of the present invention. This embodiment comprises a needle portion 92, a finger grip portion 94, a flexible fiber optic connection 96, a flexible radio frequency generator connection 98, and a length of flexible junction tubing 100.

This embodiment of the invention is similar to the previously described embodiment in that it comprises a continuous single fiber optic member extending through the entire length of the instrument. This embodiment may also comprise a stripping tool or pic 102 identical to the previously described stripping tool 50 at the distal end of the instrument. The stripping tool may be left off of the needle portion 92 if only the diathermy feature is desired.

The finger grip portion 94 of the tissue manipulator of FIG. 7 has a generally cylindrical configuration with a series of serrations 104 extending around the circumference of the grip portion to facilitate in the handling of the instrument. The grip portion 94 also has a conduit 106 extending through its interior between a distal end 108 of the grip portion and a proximal end 110 of the grip portion. The needle portion 92 is inserted into the conduit 106 at the distal end 108 of the grip portion and is held securely in the conduit by a separate plug 112 surrounding the needle portion and press-fit into the conduit 106. A distal end 114 of the flexible junction tubing 100 is inserted into and securely held in the conduit 106 of the grip portion 94 at the proximal end 110 of the portion.

Figure 8:
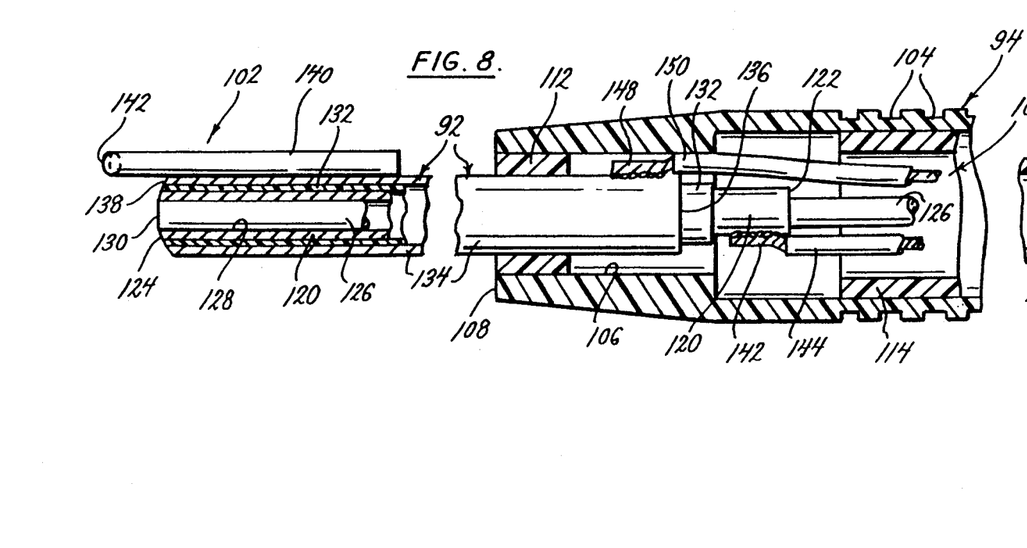
FIG. 8 is a segmented view in section of the coaxial bipolar diathermy taken along the line 8—8 of FIG. 7.

The structure of the needle portion 92 of this embodiment is shown in FIG. 8 of the drawings. The needle portion is comprised of a hollow interior needle 120 having a proximal end 122 held securely within the conduit 106 of the grip portion 94. The interior needle extends out of the distal end 108 of the grip portion, coaxial with the longitudinal axis of the grip portion, to a distal end 124.

As in the previously described embodiment, the fiber optic member 126 extends through the interior bore 128 of the interior needle 120 to its distal end 130 that is generally coplanar with the distal end 124 of the interior needle. The entire exterior surface of the interior needle 120 is covered with an insulating material 132, such as a polyamide resin, except for a portion of the exterior surface adjacent the proximal end 122 of the needle 120.

Completely surrounding the interior needle 120 and separated from the interior needle by the insulating material 132 is an exterior needle 134. The insulating material 132 prevents contact between the coaxial interior needle 120 and exterior needle 134. A proximal end 136 of the exterior needle 134 is held securely in the conduit 106 of the grip portion 94 by the plug 112. The exterior needle extends from the distal end 108 of the grip portion, coaxially with the interior needle 120 and the fiber optic member 126, to a distal end 138 located adjacent the distal end 124 of the interior needle 120 and the distal end 130 of the fiber optic member 126. The distal ends of the exterior needle 134 and the interior needle 120 are slightly rounded and therefore are not truly coplanar with the distal end 130 of the fiber optic member 126.

As in the previously described embodiment, a proximal end 140 of a pic 102 may be secured to the exterior surface of the exterior needle 134 parallel to the longitudinal axis of the needle portion 92. The stripping tool is bent at a right angle at its distal end 142.

Within the conduit 106 of the grip portion 94, the proximal end 122 of the interior needle 120 is electrically connected to an electrical conductor 142. The electrical conductor 142 is covered with an insulation 144 adjacent its connection to the interior needle 120, and the insulated conductor 142,144 extends out of the proximal end 110 of the grip portion 94, through the flexible junction tubing 100 and the flexible RF generator connection 98 to a banana plug 146 at the proximal end of the insulated electrical conductor 142,144.

A second electrical conductor 148 is electrically connected to the proximal end 136 of the exterior needle 134. This electrical conductor is also covered with an insulation 150 adjacent its connection to the proximal end 136 of the exterior needle. The insulated second conductor 148,150 extends through the conduit 106 of the grip portion and out the proximal end 110 of the grip portion, through the flexible junction tubing 100 and the flexible RF generator connection 98, to a second banana plug 152 at the proximal end of the insulated conductor 148,150.

The two banana plugs 146, 152 are provided to be inserted into output jacks of a conventional radio frequency generator. With an RF generator connected to the banana plugs, the generator can be selectively operated to supply electrical charges of different polarities to the two electrical conductors 148, 142. The electrical charges supplied to the electrical conductors are conveyed through the conductors to the exterior needle 134 and the interior needle 120, respectively. By subjecting the exterior and interior needles to electrical charges of different polarities, an electrical potential is created between the distal ends of the exterior needle 134 and the interior needle 120, providing a coaxial bipolar diathermy at the distal end of the needle portion 92 of the instrument for use in coagulating bleeding vessels on either the retinal surface or beneath pre-retinal membranes.

As in the first described embodiment, the fiber optic member 126 is a single continuous fiber that extends from its distal end 130 at the distal end of the needle portion 92, through the finger grip member 94, the flexible junction tubing 100, and the flexible fiber optic connection 96 to the connector plug 154 at its proximal end 156. The fiber optic member 126 is secured in the connector plug 154 by a short length of silicone rubber tubing 158 adjacent its distal end.

Figure 9:
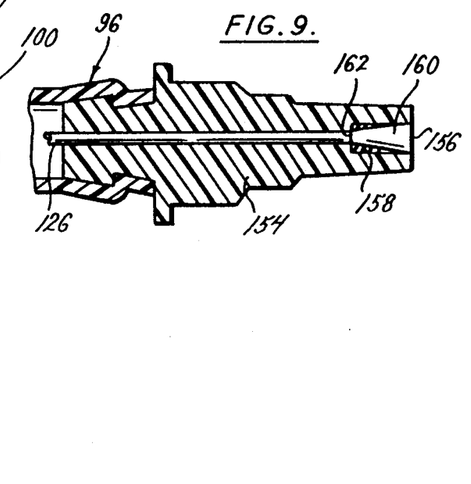
FIG. 9 is a view in section of the light source connector at the proximal end of the tissue manipulator taken along the line 9—9 of FIG. 7.

The connector plug 154 shown in FIG. 9 is another variation of the illumination source connector that can be employed with the present invention. The exterior surface of the plug is shaped to be inserted into an illumination source connection having a complementary shape.

Again, as in the first embodiment, a portion of the fiber optic member 126 adjacent its proximal end 156 is shaped in the form of a truncated cone 160 having a base coplanar with the proximal end 156 of the fiber optic member. The cone apex 162 has a diameter equivalent to the diameter of the remaining portion of the fiber optic member 126 extending between the apex 162 and the distal end 130 of the member. The silicone tubing 158 holds the cone section of the fiber optic member in the conduit of the plug 154. By subjecting the base 156 of the cone 160 at the proximal end of the fiber optic member 126 to the source of illumination, the fiber optic member 126 gathers and conveys illumination through its length to its distal end 130 where it projects a beam of light parallel to the longitudinal axis of the needle portion 92 of the instrument.

Figure 10:
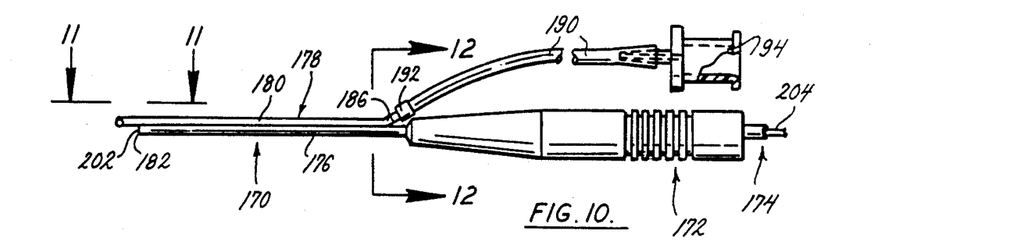
FIG. 10 is a segmented perspective view of the tissue manipulator of the present invention provided with an infusion/aspiration tube.
Figure 11:
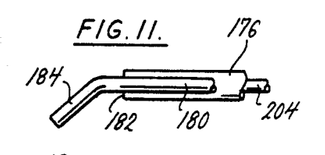
FIG. 11 is a view in section of the detail of the proximal end of the tissue manipulator of FIG. 10 taken along the line 11—11 of FIG. 10.
Figure 12:
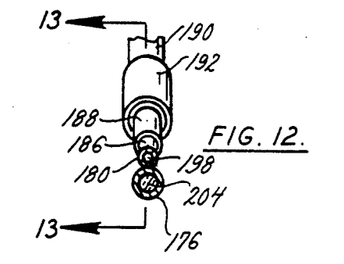
FIG. 12 is an end view in section of the tissue manipulator of FIG. 10 taken along the line 12—12 of FIG. 10.
Figure 13:
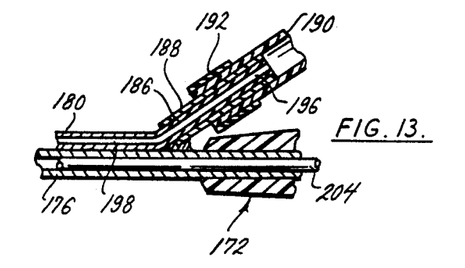
FIG. 13 is a side view in section of the tissue manipulator of FIG. 10 taken along the line 13—13 of FIG. 12.

FIG. 10 shows an embodiment of the invention comprising an infusion/aspiration system. The tissue manipulator of this embodiment of the invention is substantially identical to the tissue manipulator of FIGS. 1 and 2, except that it is not shown as comprising a stripping tool at its distal end. The tissue manipulator of FIG. 10 comprises a needle portion 170, a finger grip portion 172, and a flexible fiber optic connection 174 extending to an illumination source connector (not shown). The structures of these components are identical to those described with reference to the first embodiment of the invention shown in FIGS. 1 and 2.

Attached to an exterior surface of the needle 176 is an infusion/aspiration assembly. The assembly includes a three-section hollow pipe 178 having an intermediate section 180 secured to the needle 176 parallel to the longitudinal axis of the needle portion and finger grip portion. The intermediate section 180 of the pipe extends a small distance past the distal end 182 of the needle 176 to a distal section 184 of the pipe. The distal section 184 of the pipe is angled at about 45° from the longitudinal axis of the intermediate section 180 of the pipe. Both the distal section 184 and the intermediate section 180 of the pipe are positioned in a plane that runs parallel to the longitudinal axis of the needle portion 170 of the instrument but does not intersect this axis.

A proximal section 186 of the pipe is connected to the intermediate section 180 opposite to its connection to the distal section 184. The proximal section 186 extends off from the intermediate section 180 at an angle of 45° to the longitudinal axis of the intermediate section. The proximal section 186 is surrounded by an adapter sleeve 188 that, in turn, is inserted into a length of flexible tubing 190. The flexible tubing 190 is secured in a seal-tight connection to the adapter sleeve 188 by a connector band 192 securely fastened around the flexible tubing 190, the adapter sleeve 188, and the proximal end 186 of the pipe.

The opposite end of the flexible tubing 190 is connected with an adapter assembly 194 that is dimensioned to be connected with a conventional infusion or aspiration source. By selectively supplying fluid under pressure to the adapter assembly 194, the fluid is conveyed through the flexible tubing 190 to the center bore 196 of the proximal pipe section 186. The fluid passes through the proximal section bore 196 to the intermediate section bore 198, and through the intermediate section bore 198 to the distal section bore from which it is dispensed from the infusion/aspiration three-section pipe 178. The three section pipe can also be connected to a source of suction to provide aspiration at the distal section of the pipe.

This embodiment of the present invention provides a means of supplying fluid or a suction at the distal end of the instrument without obstructing the beam of light projected from the distal end 202 of the fiber optic member 204 extending through the instrument.

FIGS. 14-17 show a still further embodiment of the present invention comprising an infusion/aspiration system. This embodiment includes a needle portion 206, a finger grip portion 208, and a flexible fiber optic connection 210. The finger grip portion 208 of this embodiment is comprised of a front 212 and back 214 section. The front section 212 of the grip portion has a generally cylindrical exterior surface and an interior conduit extending through the section between its proximal end 216 and its distal end 218.

Figure 14:
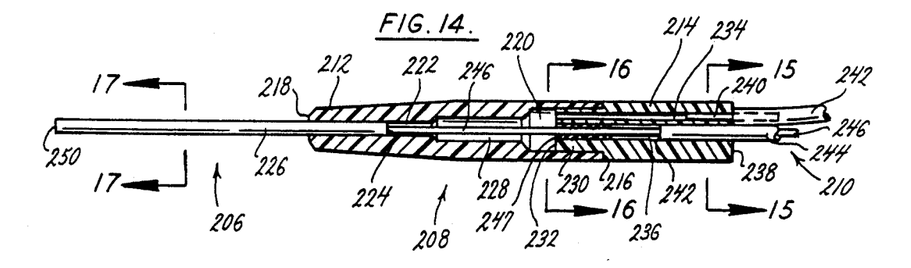
FIG. 14 is a plan view in section of the tissue manipulator of the present invention with in infusion passage passing through the manipulator.
Figure 15:
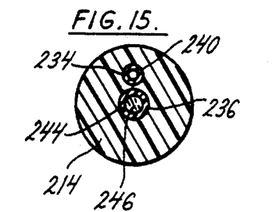
FIG. 15 is a cross-section view of the tissue manipulator of FIG. 14 taken along the line 15—15 of FIG. 14.
Figure 16:
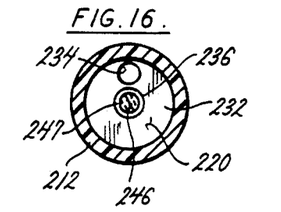
FIG. 16 is a cross-section view of the tissue manipulator of FIG. 14 taken along the line 16—16 of FIG. 14.

The interior conduit of the front section 212 is comprised of three cylindrical chambers. A first chamber 220 of the interior conduit is positioned adjacent the proximal end 216 of the front section and has the largest interior diameter of the three chambers. The second chamber 222 is positioned adjacent the distal end 218 of the front section and has a diameter large enough to receive the proximal end 224 of the needle 226 and hold the needle securely in place extending from the distal end 218 of the front section. The third chamber 228 of the interior conduit is positioned intermediate the first and second chambers and has an interior diameter intermediate the diameters of the first and second chambers.

The back section 214 of the grip portion of the instrument also has a generally cylindrical exterior surface with a portion 230 of the back section 214 adjacent the distal end 232 of the back section having a reduced outside diameter. The reduced diameter portion 230 of the back section 214 is inserted into and secured in place in the first chamber 220 of the front section 212. The back section 214 also has first and second conduits 234,236 extending through its length between the distal end 232 of the section and the proximal end 238 of the section.

A tubular adapter 240 is inserted into the first conduit 234 at the proximal end 238 of the back section 214. A flexible tube 242 of a conventional infusion/aspiration system is connected with the tubular adapter 240 establishing fluid communication between the infusion/aspiration system and the first chamber 220 of the grip portion 208.

The second conduit 236 is coaxial to the finger grip portion 208 and the needle portion 206 of the instrument. A flexible fiber optic connection 210 of the type described with reference to the first embodiment is inserted in the second conduit 236 at the proximal end 238 of the back section 214. The diameter of the second conduit is dimensioned large enough to securely receive the distal end 242 of the insulating tubing 244, surrounding the fiber optic member 246 of the flexible fiber optic connection 210. The fiber optic member 246 extends beyond the distal end 242 of the insulating tubing and through a tubular sleeve 247 that is press-fit into the second conduit 236 at the distal end 232 of the back section 214. The sleeve forms a fluid seal between the fiber optic member 246 and the second conduit 236. The fiber optic member extends from the sleeve 247 through the first chamber 220, the third chamber 228, and the second chamber 222 of the front section of the grip member 208, and through the interior bore 248 of the needle 226 of the instrument needle portion 206. The distal end 250 of the fiber optic member 246 terminates coplanar with the distal end of the needle 226.

Figure 17:
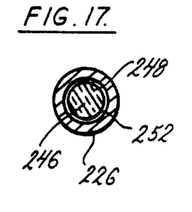
FIG. 17 is a cross-section view of the tissue manipulator of FIG. 14 taken along the line 17—17 of FIG. 14.

As best seen in FIG. 17, the outside diameter of the fiber optic member 246 is slightly smaller than the interior diameter of the needle bore 248. This difference in the diameters of the fiber optic member and the needle interior bore creates an open passage 252 extending along the length of the interior bore of the needle and the exterior surface of the fiber optic member contained within the bore of the needle.

By selectively supplying either pressurized fluid or suction to the flexible tubing 242 from a conventional infusion/aspiration system, the fluid or suction is transmitted through the tubular adapter 240, the first conduit 234, the first chamber 220, the third chamber 228, the second chamber 222, and the open passage 252 between the interior bore 248 of the needle 226 and the exterior surface of the fiber optic member 246 to the distal end 250 of the needle portion 206 of the instrument.

With this assembly, fluid infusion or aspiration is provided at the distal end 250 of the needle portion of the instrument in addition to the illumination supplied at the distal 250 of the needle provided by the fiber optic member 236 proximal end being selectively illuminated by a source of light.

Although the component parts of the present invention have been described above by reference to specific embodiments of the invention employing two or more of the component parts of the invention, it should be understood that these embodiments are only illustrative and that modifications and variations of the invention that comprise one or all of the component parts of the invention described above may be constructed without departing from the scope of the invention defined in the following claims:

What is claimed is:

1. A method of penetrating and working in the vitreous humor of the eye comprising:

gripping a finger grip member of a surgical instrument, the grip member having first and second ends, and a conduit extending through the grip member;

inserting the tip end of a needle into the vitreous humor of the eye, the needle having first and second ends, the first needle end being insertable into the vitreous humor, and the second needle end being securely attached to the first end of the grip member;

illuminating the area of the vitreous humor adjacent the first needle end by light directed through a fiber optic member extending from a source of illumination through the conduit and the needle, the fiber optic member being co-axial with the needle;

working in the vitreous humor with a pic secured to the first needle end, the pic being parallel to, but spaced apart from, a longitudinal axis of the fiber optic member and needle; and, applying an electrical current to the area adjacent the tip end of the needle to coagulate any blood occurring thereat, said electrical current being applied through a first conducting member which is a tubular member coaxial with and immediately surrounding the fiber optic member, and a second conducting member which is a tubular member coaxial with and outside of said first conducting member, said first and second conducting members being spacially separated by an electrically insulating member located between the two conducting members.

2. The method of claim 1 wherein applying the electrical current includes applying a radio frequency signal to the respective first and second conducting members.

* * * * *